(12) United States Patent
Hanisch et al.

(10) Patent No.: US 8,062,034 B2
(45) Date of Patent: Nov. 22, 2011

(54) DEVICE FOR SELECTING AN AREA OF A DENTAL RESTORATION BODY, WHICH IS DEPICTED IN A 3D REPRESENTATION, AND METHOD THEREFOR

(75) Inventors: Heinrich Hanisch, Gross-Zimmern (DE); Ulrich Orth, Lautertal (DE); Volker Wedler, Hirschberg (DE)

(73) Assignee: Sirona Dental Systems GmbH, Bensheim (DE)

( * ) Notice: Subject to any disclaimer, the term of this patent is extended or adjusted under 35 U.S.C. 154(b) by 577 days.

(21) Appl. No.: 10/547,680

(22) PCT Filed: Mar. 5, 2004

(86) PCT No.: PCT/DE2004/000448
§ 371 (c)(1),
(2), (4) Date: Sep. 2, 2005

(87) PCT Pub. No.: WO2004/078058
PCT Pub. Date: Sep. 16, 2004

(65) Prior Publication Data
US 2006/0155404 A1 Jul. 13, 2006

(30) Foreign Application Priority Data
Mar. 5, 2003 (DE) .................................. 103 09 839

(51) Int. Cl.
*A61C 5/00* (2006.01)
*G06F 19/00* (2011.01)
(52) U.S. Cl. ......................................... 433/215; 700/98

(58) Field of Classification Search .................... 433/24, 433/172, 215, 202.1, 204, 223; 700/97–98, 700/163, 219
See application file for complete search history.

(56) References Cited

U.S. PATENT DOCUMENTS

| 5,273,429 | A | 12/1993 | Rekow et al. |
| 5,417,572 | A | 5/1995 | Kawai et al. |
| 6,049,743 | A | 4/2000 | Baba |
| 6,694,212 | B1 * | 2/2004 | Kennedy ........................ 700/163 |
| 2002/0110786 | A1 * | 8/2002 | Dillier ........................... 433/213 |
| 2003/0207235 | A1 | 11/2003 | der Zel |

* cited by examiner

*Primary Examiner* — Cris L Rodriguez
*Assistant Examiner* — Heidi M Eide
(74) *Attorney, Agent, or Firm* — Fitzpatrick, Cella, Harper & Scinto (57) ABSTRACT

The invention relates to a device for selecting an area (2; 22; 32; 42; 52; 62; 72; 82) of a dental restoration body (1;71), which is depicted in a 3D representation. At least portions of the area limit are provided in the form of dental-specific lines (5, 6, 8). The aim of the invention is to carry out a dental construction of a restoration body with the aid of a CAD system, whereby certain areas of the restoration body can be selected and construction tools are provided for machining the selected area in a 3D representation. To this end, the area (2; 22; 32; 42; 52; 62; 72; 82), which is to be machined with a construction tool, can be determined by selecting dental-specific lines (5, 6, 8) or dental-specific points (7.1 7.4) or a preparation edge (4). The method is used for assigning area limits to the selected area, said area limits being provided, at least in part, in the form of dental-specific lines (5, 6, 8).

16 Claims, 10 Drawing Sheets

DEVICE FOR SELECTING AN AREA OF A DENTAL RESTORATION BODY, WHICH IS DEPICTED IN A 3D REPRESENTATION, AND METHOD THEREFOR

BACKGROUND OF THE INVENTION

The invention relates to a device for the selection of a region of a dental restoration body depicted in 3β representation and a method therefor.

DESCRIPTION OF THE RELATED ART

The prior art includes CAD/CAM systems for the design and fabrication of tooth restoration bodies, which, by means of a preparation image of a prepared tooth, use teeth from a tooth data base in the form of characteristic lines such as the preparation border, equator, marginal crest, and fissure, in order to design and fabricate a restoration body.

In order to improve fitting accuracy, provision is also made for at least part of the occlusal surface of a tooth present in the data base to be transferred, by copying, to the restoration body to be fabricated.

For specific modification of a dental design with the help of a CAD system it is always necessary to select those regions that are to be processed with specific design tools.

In the prior art, selection of the region is executed by way of a menu or dialog. In addition, the region can be defined by drawing in a boundary line.

This suffers from the drawback that the boundaries of the regions to be modified and thus of the designed tooth shapes, are not dentally specific.

SUMMARY AND OBJECTS OF THE INVENTION

In accordance with the invention, the region is defined by selection of dentally specific lines or of dentally specific points or of a preparation border.

This has the advantage that the system can be operated in a simple and intuitive manner while working directly on the image to be modified. Therefore the region to be worked on is selected intuitively by selecting a line or a point that is associated with a typically dental region.

It is advantageous if the restoration to be designed, ie the tooth that is to be fabricated, is divided into regions that are, at least in part, delimited by dentally specific lines and are indicated in the three-dimensional representation of the restoration.

Suitable dentally specific lines are the equator and the marginal crest, or alternatively with anterior teeth, the labio-lingual line and the fissure, or again alternatively with anterior teeth, the cutting edge, and suitable dentally specific points are the position of one or more cusp peaks, individually or severally or all together.

Advantageously, each dentally specific line and/or preparation border is divided into four parts representing the mesial, distal, buccal, and lingual sides of the tooth respectively. This makes it possible to allocate the region to be selected.

Advantageously, the selected part of the line determines the part of the tooth in which the region is located. Thus selection is effected directly with reference to that side of the three-dimensional representation which is displayed.

In accordance with a further advantageous development, the selected line defines the whole region in accordance with the following assignments:

preparation border: the region extends from the preparation border to the center of the occlusal surface;
equator: the region is located between the preparation boundary and the marginal crest;
marginal crest: the region extends from the equator to the center of the occlusal surface;
fissure: the entire occlusal surface is selected as the region, which is delimited by the marginal crest.

Selection of a line will clearly define the region assigned to it.

Advantageously, by selecting a dentally specific point identifying the position of a cusp peak, the region of the respective cusp can be selected as far as its cusp borders, whilst the lower border of the region can be formed by the equator.

In accordance with a further development, the selected region is depicted in a distinguishable fashion.

In accordance with a further development, means for evaluating and/or comparing geometrical data of the selected region are provided. This makes it possible to store the selected region in memory or to compare it with a region of another restoration or any other tooth stored in memory.

In accordance with a further development, the selected region can be processed with the aid of a design tool of a CAD system. The region to be processed with the design tool is defined by selecting dentally specific lines or dentally specific points or a preparation border.

Advantageously, the tool adapted to modify the region leaves the boundaries of the region unchanged, whilst a continuous increase in modification takes place toward the point requiring the greatest degree of modification. This enables systematic processing of the selected region whilst allowing for dentally specific requirements.

Advantageously, the point requiring the greatest degree of modification is located on a dentally specific line or at a dentally specific point. This ensures that processing with the design tool will not make unexpected modifications in regions not receiving the attention of the operator.

The invention further relates to a method of selecting a region of a dental restoration body depicted as a 3D representation, in which boundaries are assigned to the selected region which are, at least in part, defined by dentally specific lines. This has the advantage that the selection of a region conforms to dentally specific requirements and can easily be consulted for subsequent treatment of the region or for the purpose of comparative analysis.

Advantageously, selection of the region is effected by selecting a dentally specific line or a dentally specific point or a preparation border associated with the region to be selected. Such a selection has the advantage that it is clear to the user which region he or she is momentarily selecting.

BRIEF DESCRIPTION OF THE DRAWINGS

The device of the invention is explained below with reference to the drawings, in which.

DETAILED DESCRIPTION OF EXEMPLARY EMBODIMENTS OF THE INVENTION

In a CAD system, dentally specific lines and points are depicted in a 3D representation of the restoration. By clicking on individual elements, a region to be processed using design tools, for example, is selected, and the user can immediately begin work thereon within the representation to be processed. The design tool used can, in particular, be a shaping tool which changes the shape of a surface from the boundary of the region up to the point requiring the greatest degree of modification.

Figure 1:
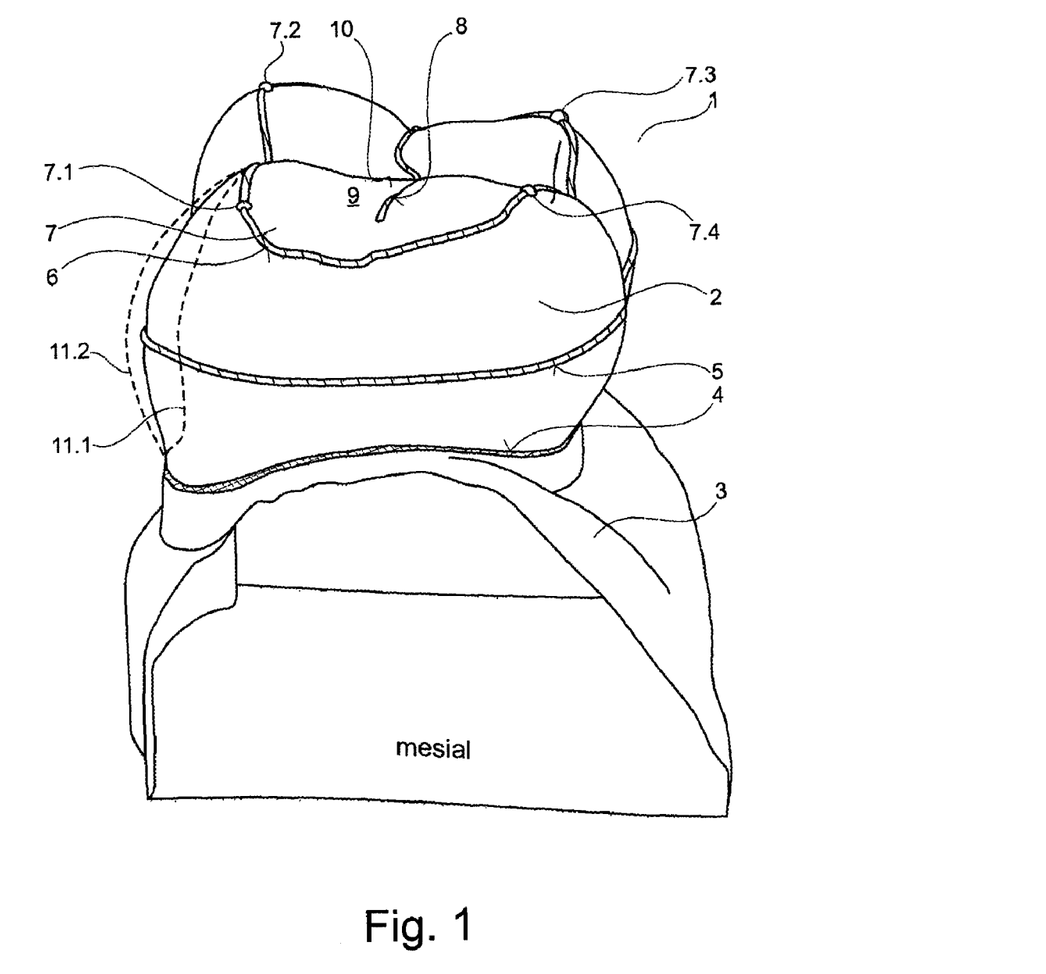
FIG. 1 illustrates a restoration body in the form of a molar, showing its mesial side with a selected region corresponding to the anterior half of the tooth.

FIG. 1 shows a restoration body to be fabricated in the form of a molar 1 showing its mesial side, a region 2 corresponding to the anterior half of the tooth being selected. In the 3D representation of tooth 1, the unselected region is shown as a hatched region, and, in addition, several lines and points are indicated, which will be described below.

Starting from the lower, cervical end of tooth 1, which is located in the region of the gingiva 3, a first line is shown in the form of the preparation border 4. The preparation border 4 represents the boundary between the original tooth surface in its unprepared condition and the prepared part of the tooth.

In the region of the largest circumference of tooth 1, the equator 5 is drawn as one of several dentally specific lines. Progressing to the top of tooth 1, a marginal crest 6 is drawn in, which extends across tooth cusps 7 particularly characterized by dentally specific points 7.1 to 7.4.

Another dentally specific line is a fissure 8, which extends along the surface of tooth 1 within an occlusal surface 9 delimited by marginal crest 6.

Another regional boundary is a dividing line 10 between the anterior mesial half and the posterior distal half of tooth 1, which may correspond to the course of a lateral fissure, but may simply represent a way of imparting geometrical information. The course of this line in the representation described herein is of secondary dental importance.

The region 2 will be selected by selecting the preparation border 4, for example by a mouse click, and it will extend from preparation border 4 up to the center of occlusal surface 9, which is indicated by the course of line 10.

Obviously, instead of clicking on preparation border 4, provision can be made for selection to be effected by clicking on the regions between the previously described lines or points. For example, the tooth half represented in FIG. 1 can be selected by clicking on the region between preparation border 4 and equator 5. Clicking on other regions in the representation leads to selection of a differently delimited region.

Using a processing tool, the entire region 2 can be processed, and, by entering keyboard commands, for example, its size can be enlarged or reduced horizontally, vertically, or normal to the plane of display. The region can therefore be modified in all six directions in space, suggested by the lines 11.1 and 11.2 indicating reduction and enlargement of the width of the tooth respectively.

The same applies, of course, to the height of the tooth and its spatial dimensions extending towards and away from the user. Such modifications will also change the course of fissure 8.

Figure 2:
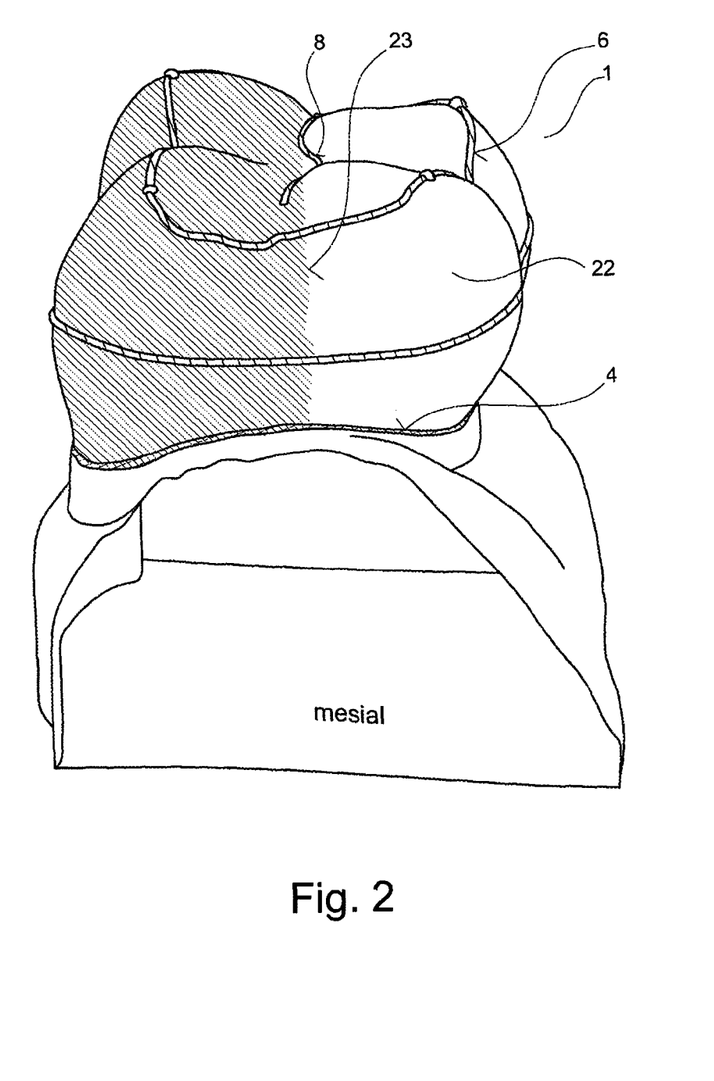
FIG. 2 shows the tooth of FIG. 1 but with the right-hand half of the tooth being the selected region.

In FIG. 2, tooth 1 is represented from the same direction as in FIG. 1, but in this case the right-hand lingual half of the tooth is the selected region 22. In this representation it is particularly easy to recognize that a boundary line 23 of the selected region 22 is not a typical dental design line but only an auxiliary line for demarcation of the region 22. The line 23 runs approximately through the center of tooth 1 and thus approximately within the region of the lateral fissures. The lateral fissure can, of course, also be used as a dentally specific line for delimiting region 22 if it has been allocated for this purpose by the measuring data or in some other way.

If the selected region 22 is processed with a tool for CAD purposes, then preparation border 4 and auxiliary line 23 will remain unchanged.

Figure 2A:
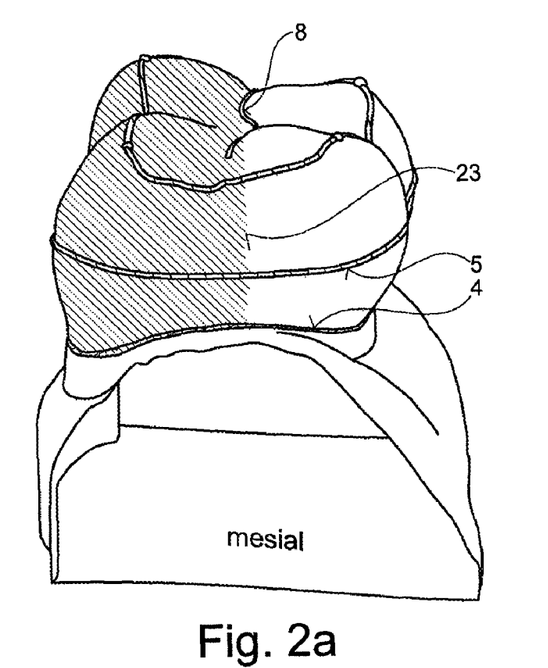
FIGS. 2a and 2b show the tooth of FIG. 2 with the right-hand half of the tooth as the selected region and comparing the pre-modified state (FIG. 2a) with the post-modified state (FIG. 2b)
Figure 2B:
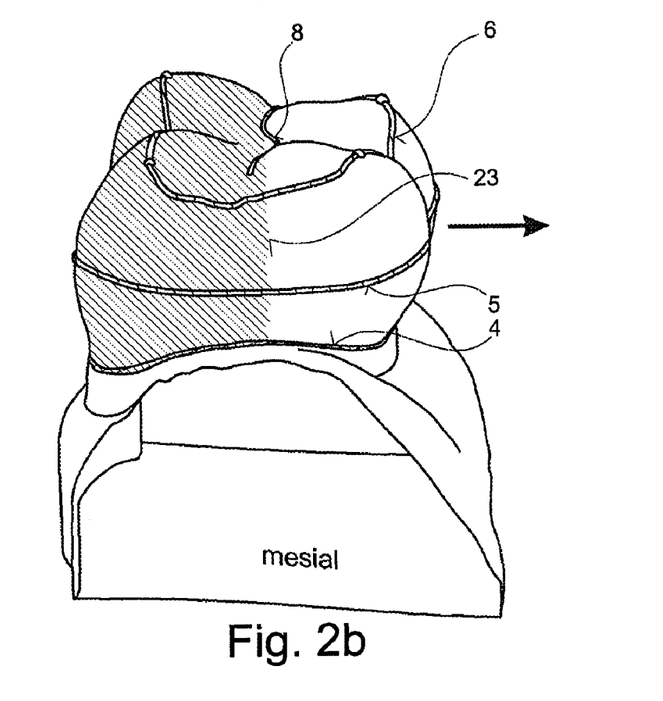

FIGS. 2a and 2b show the tooth of FIG. 2 with its right-hand half being the selected region and provide means of comparison between a pre-modified state (FIG. 2a) and a post-modified state (FIG. 2b), modifications having been made in the direction of the arrows. The course of preparation border 4 and line 23 have not changed, but equator 5, marginal crest 6, and the fissure have changed their position in the direction of the arrows.

Figure 3:
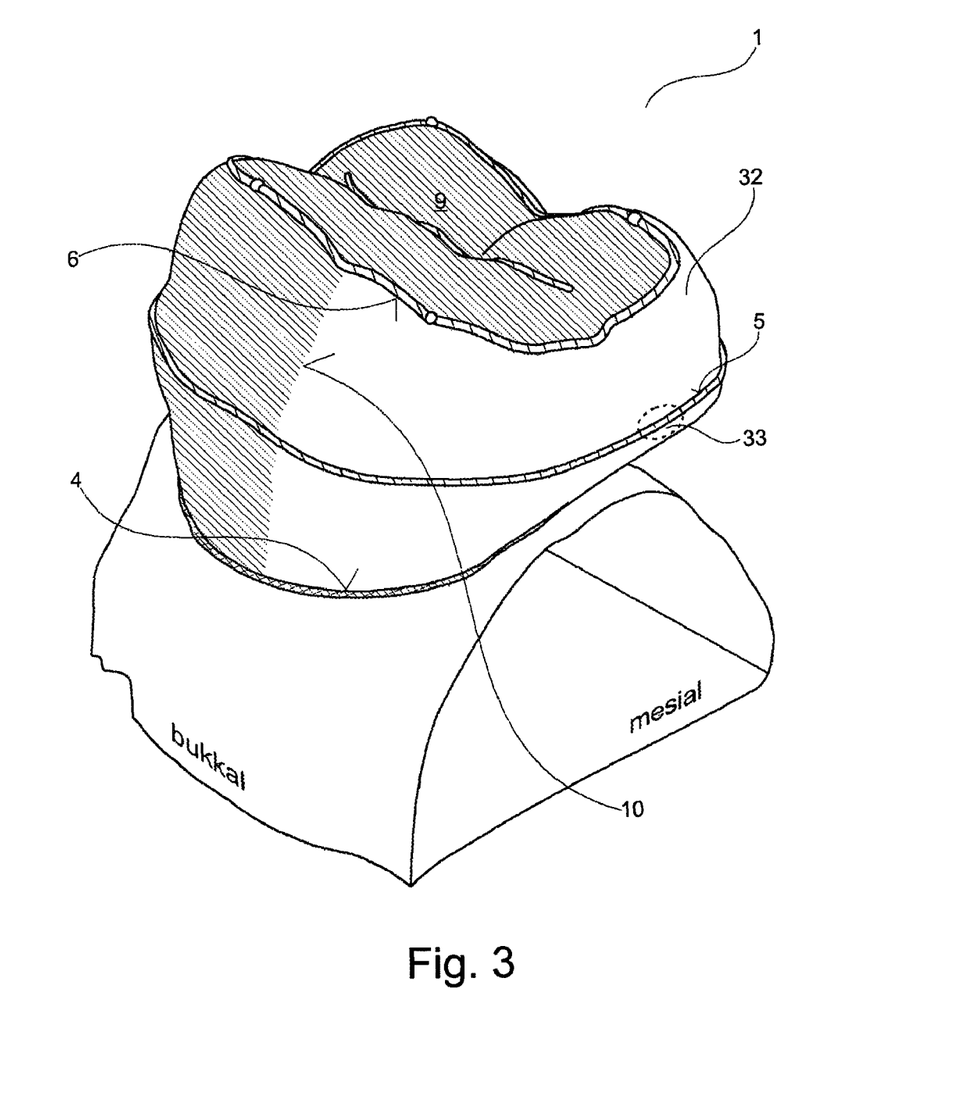
FIG. 3 shows the tooth of FIG. 1 viewed from an oblique angle with the selected region being a lateral surface of the anterior half of the tooth.

In FIG. 3, tooth 1 is represented in an oblique view, whilst the selected region 32 of interest represents the lateral surface of the anterior half of tooth 1 of FIG. 1. The occlusal surface 9, in contrast to FIG. 1, is therefore no longer part of the selected region 32. The selected region 32 is delimited by preparation border 4, auxiliary line 10, and marginal crest 6.

If region 32 is now processed with the design tool, only the lateral surface will expand in the mesial direction, for example, without marginal crest 6, auxiliary line 10, or preparation border 4 being modified.

Modifications in the course of the surface will take place in such a way that the modification, starting from modification "zero" at the previously described boundaries of region 32 up to the point of greatest modification, indicated by the hatched circle 33, gradually increases in the mesial direction during the shaping operation, so that the surface within the entire region 32, with exception of the boundary region, is modified. Region 32 is selected, for example, by clicking on equator 5.

Figure 4:
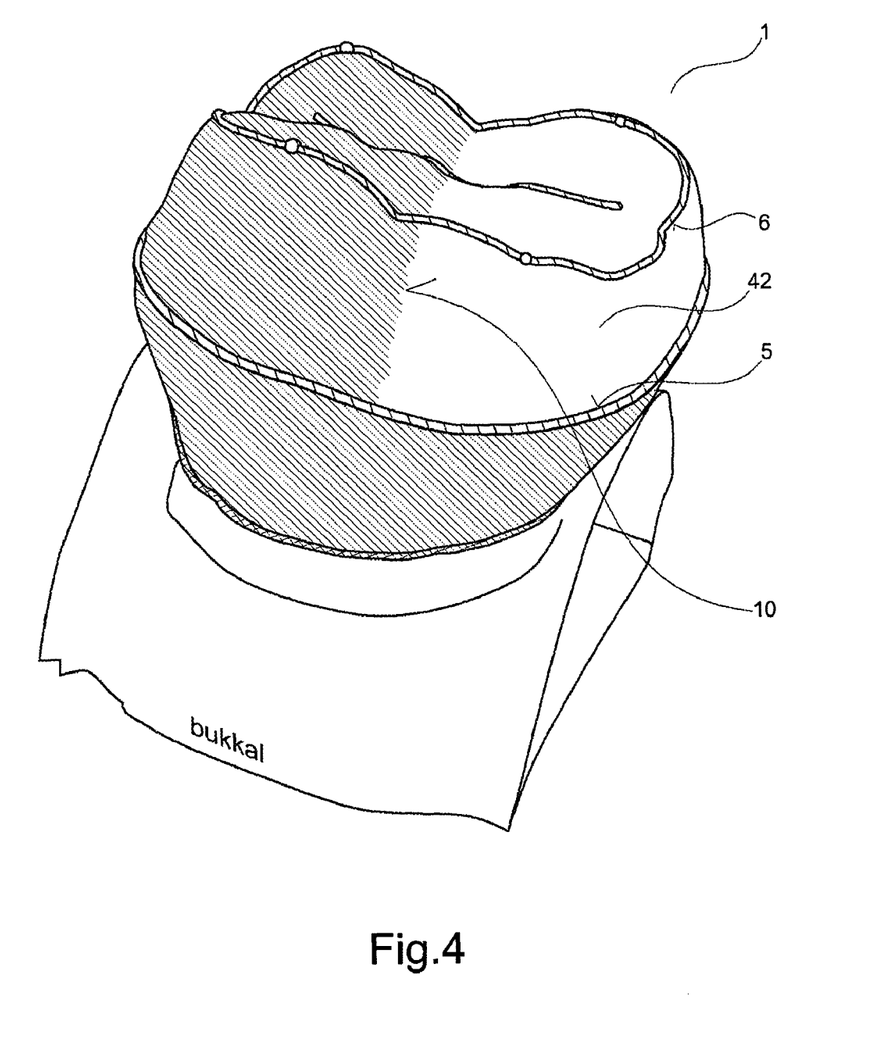
FIG. 4 illustrates the tooth of FIG. 1 showing its buccal side with the selected region being the surface of the forward region of the tooth above the equator.

In FIG. 4, tooth 1 of FIG. 1 is illustrated showing its buccal side and the selected region 42 covers only the surface of the anterior region of the tooth above equator 5. The boundaries of the selected region 42 are therefore defined by equator 5 and auxiliary line 10. Auxiliary line 10 approximately coincides with the lateral fissures, but its exact course is not of crucial importance in this case. Selection of region 42 is effected, for example, by clicking on the right-hand part of marginal crest 6.

Figure 5:
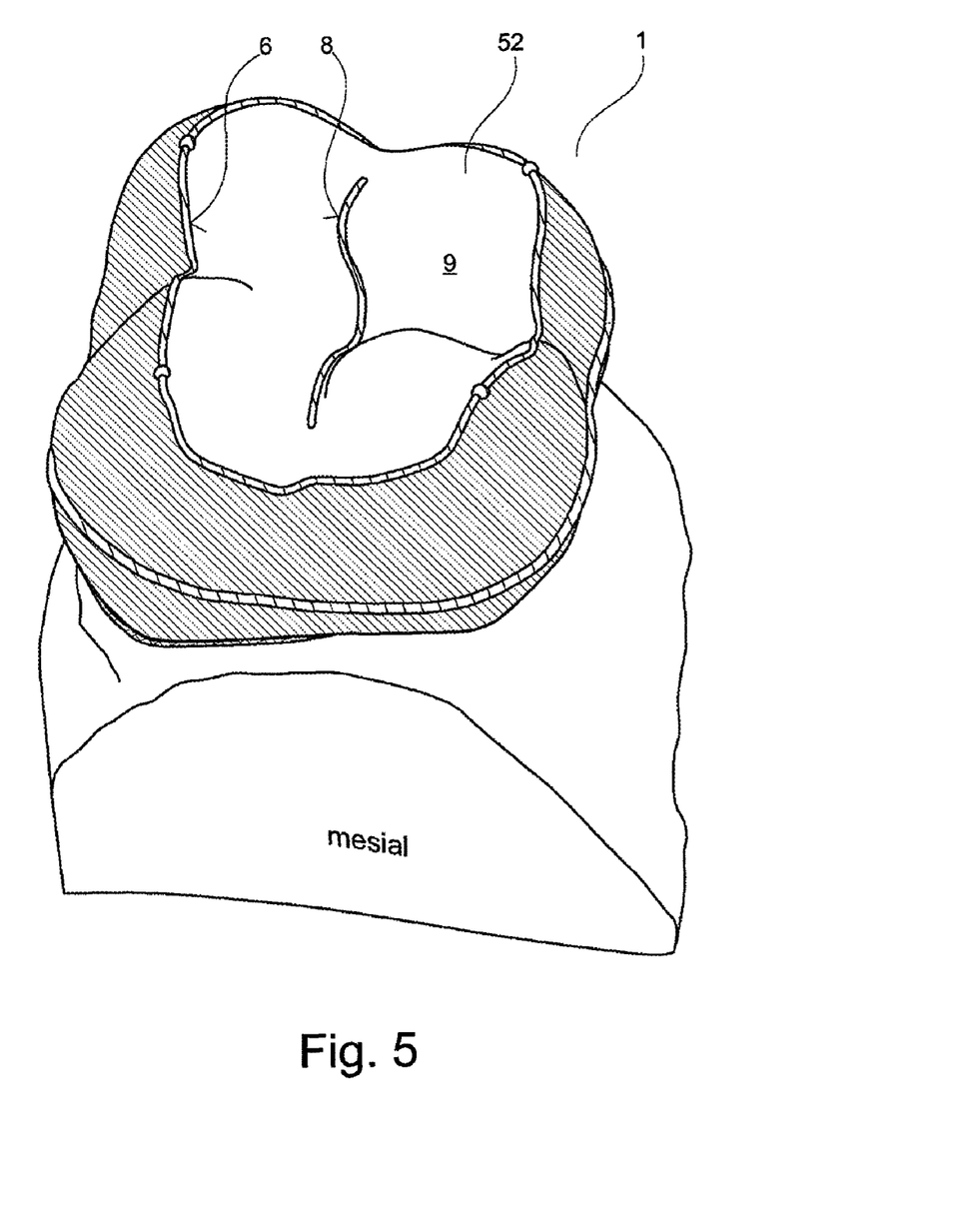
FIG. 5 illustrates the tooth of FIG. 1 showing its mesial side from above with the occlusal surface as the selected region.

In FIG. 5, tooth 1 of FIG. 1 is illustrated showing its mesial side viewed obliquely from above and the selected region 52 is the occlusal surface 9. Occlusal surface 9 is delimited by marginal crest 6. Modifications only affect the position, but not the course, of fissure 8. This means that the spatial relationship between the points forming the fissure 8 does not change, ie, in particular, that the line is not stretched or bent. The entire line will be raised or lowered, for example, as occlusal surface 9 is modified.

Figure 6:
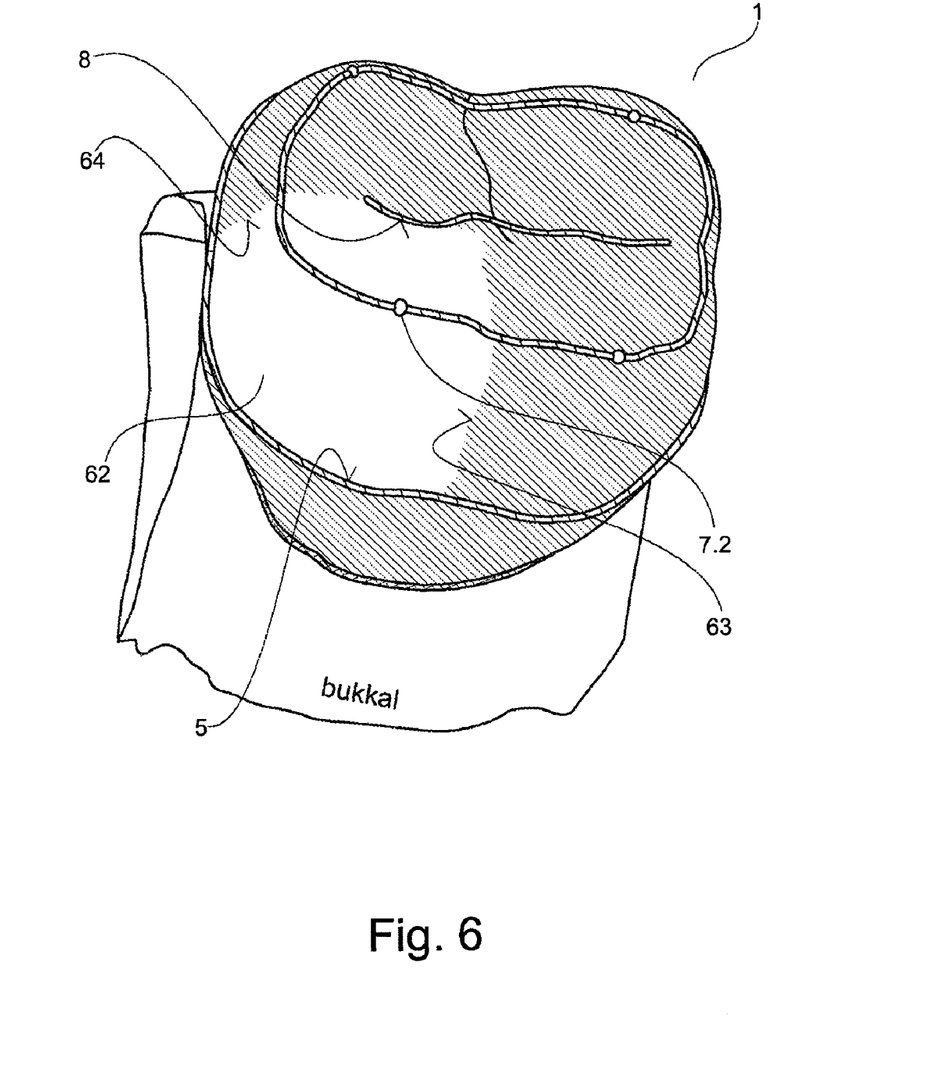
FIG. 6 illustrates the tooth of FIG. 1 showing its buccal side viewed from an oblique angle with a cusp being the selected region.

FIG. 6 illustrates the tooth of FIG. 1 showing its buccal side from an oblique angle, and a cusp, identified by point 7.2, is represented as the selected region 62. The selected region 62 including the cusp is delimited at the bottom by equator 5 and laterally by the cusp borders 63 and 64. The boundary 64 runs along fissure 8 and an extension thereof and merges with the lateral fissure, and cusp boundary 63 consists of the lateral fissure and its extension.

The cusp peak 7.2 can be processed together with the rest of the surface in all six directions in space. Thus it can be raised or lowered, shifted in the distal and mesial directions, and likewise in the buccal and lingual directions. Here again, the boundaries of region 62 remain unchanged. Selection of region 62 is effected, for example, by clicking on point 7.2.

Figure 7:
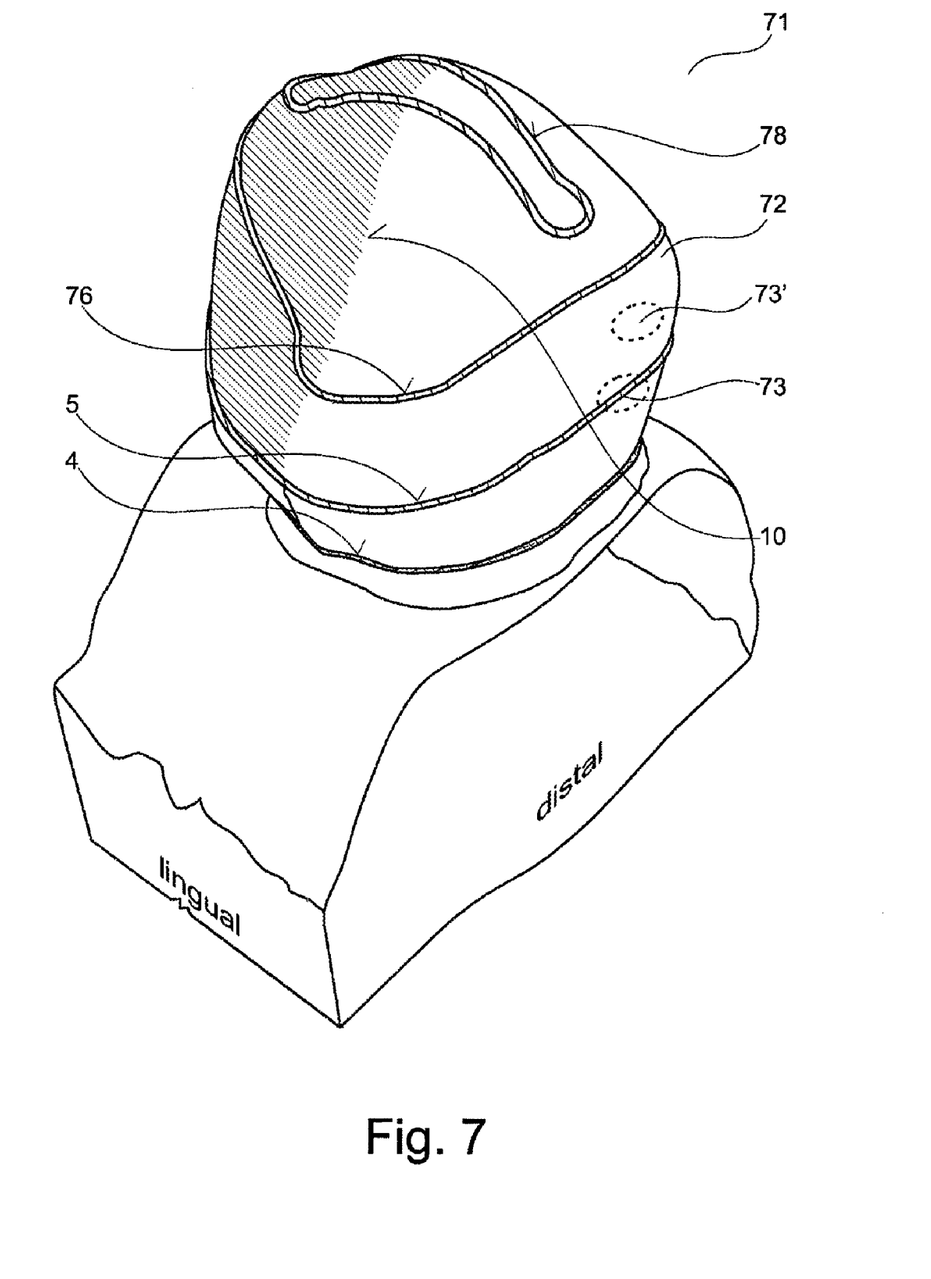
FIG. 7 illustrates a restoration body in the form of an anterior tooth showing its lingual and distal sides viewed from an oblique angle with one half of the tooth being the selected region.

FIG. 7 depicts an anterior tooth 71 as an oblique view of its lingual and distal sides. One half of tooth 71 is represented as a selected region 72. At the tip of the tooth 71 there is shown the cutting edge 78, which encompasses the region of the incisor edge.

In addition, the auxiliary line 10 that divides tooth 71 into two halves is shown. The selected region 72 is thus delimited by preparation line 4 and auxiliary line 76, and the surface of region 72 can be modified in all six directions in space, whilst no change takes place at the regional boundaries and, again, a constantly increasing modification up to the point of greatest modification, as indicated by the hatched circle 73, takes place when making modifications in the distal direction.

Region 73 requiring the greatest degree of modification lies on a dentally specific line, ie, on equator 5. Even if other regions 73' are present that are further removed from a center or a central axis, they are deformed to a lesser extent by use of the design tool. This also applies to the other exemplary embodiments.

Figure 8:
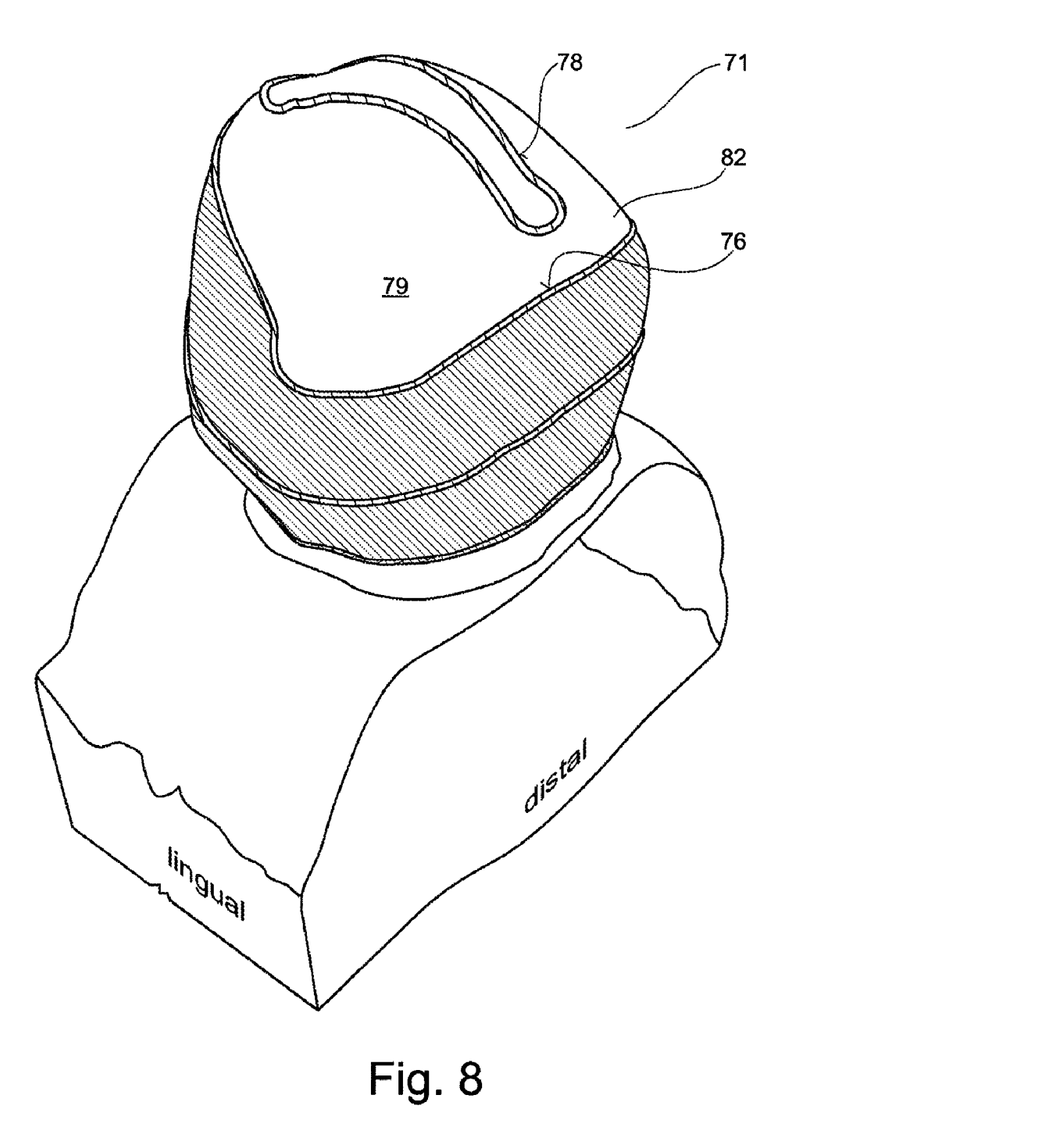
FIG. 8 illustrates the tooth of FIG. 7 with the occlusal region above the labiolingual line being the selected region.

FIG. 8 shows tooth 71 of FIG. 7 from the same viewpoint, but in this case occlusal surface 79 above labiolingual line 76 is selected.

Modifications within this region 72 also affect cutting edge 78, as has already been explained with reference to the modification of the occlusal region in respect of FIG. 5. The position of the cutting edge 78 can be changed, but not its course as such.

In principle, the dentally specific design lines are proposed by the CAD system on the basis of the existing 3D data set and can also be adapted by hand to account for dentally specific problem definitions. This applies to dentally specific points as well as to the positions of cusp peaks.

Each line 4, 5, 6 is divided into four parts representing the mesial, distal, buccal, and lingual sides of the tooth respectively. By selecting a subregion of the line, for example by clicking, that half of the tooth is specified in which the selected region lies.

Depending on which of the lines is selected, a respective region of the tooth is selected. Selection of preparation border 4 causes region 2, 22 extending from preparation border 4 to the center of occlusal surface 9 to be selected. Selection of equator 5 causes the region 32 located between the preparation border and marginal crest 6 to be selected. Selection of marginal crest 6 causes the region 42 extending from equator 5 to the center of the occlusal surface to be selected, and selection of fissure 8 causes the entire occlusal surface 9 to be selected as region 52, delimited by marginal crest 6.

As has already been noted in the description of FIG. 1, a region can also be selected by clicking the surface of the tooth representation in places other than the dentally specific lines or dentally specific points. Clicking on a tooth cusp in the region of its peak can result in selection of the tooth cusp. Clicking on a region between two cusps can lead to the selection of the entire occlusal surface. Clicking on the surface between the equator and the marginal crest can result in selections as shown in FIG. 3 or FIG. 4, depending on whether the region is selected closer to the equator or to the marginal crest. Here again, it is necessary for the surface to be divided into mesial, distal, buccal, and lingual sides of the tooth, so that the respective region of interest will be clearly defined.

Similarly, in the case of an anterior tooth, selection of the region represented in FIG. 7, for example, can be followed by clicking on a region below the labiolingual line, which will result in a selection as shown in FIG. 8. If, then, a region below the labiolingual line is selected, a selection ensues as shown in FIG. 7.

Figure 9:
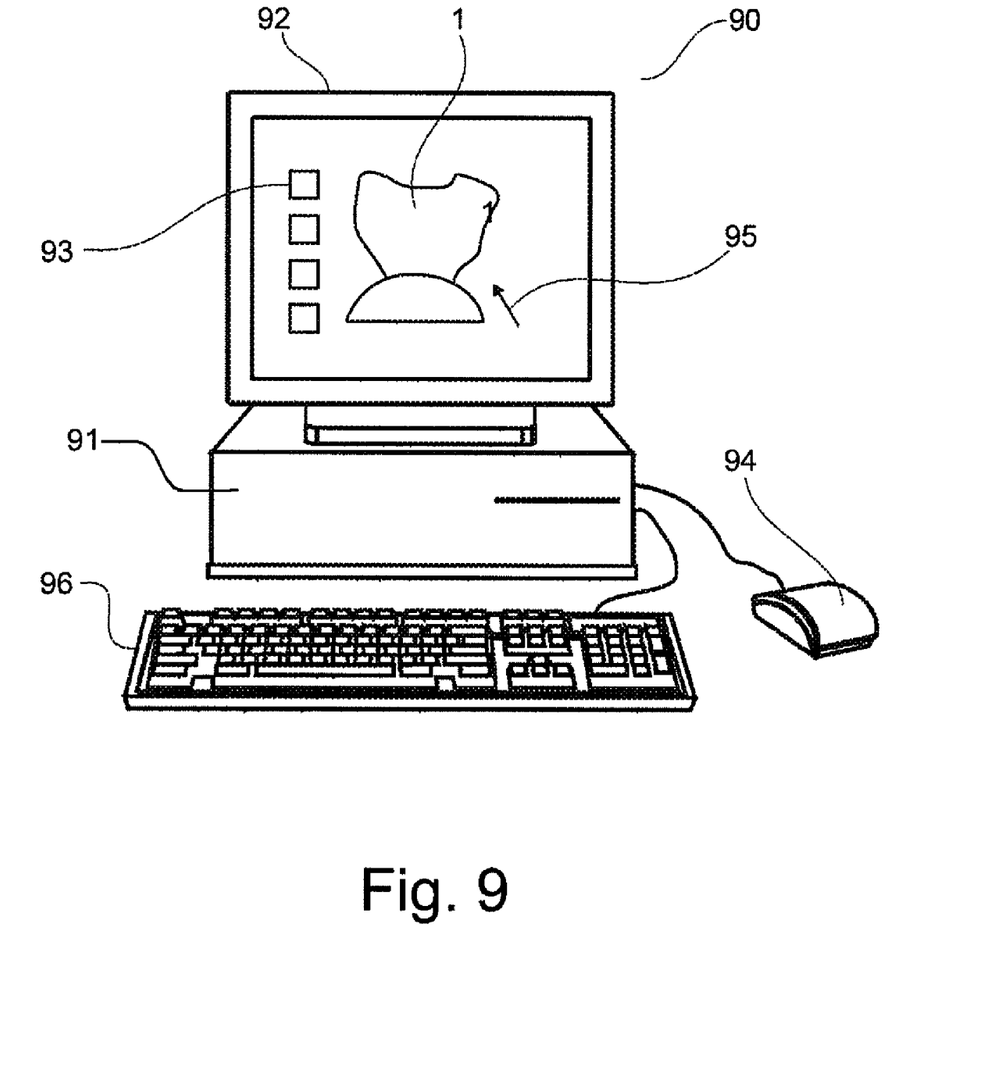
FIG. 9 illustrates the fundamental parts of the device.

FIG. 9 illustrates the fundamental configuration of the device. The device includes a CAD system 90 with a computer 91 and a display unit 92 for the representation of restoration body 1 and for the selection of a design tool 93 represented by symbols. Furthermore, an input unit in the form of a computer mouse 94 is available for the control of a pointer 95 displayed on display 92. In addition or alternatively, a keyboard 96 is provided for inputting control commands into the computer 91.

The invention claimed is:

1. A computer-aided design (CAD) system comprising:
    a computer;
    a display device that is directed by the computer to display an image of a dental restoration body, the dental restoration body including a plurality of distinct dentally specific indicia, each indicium being a single, selectable, unique type of dental feature that is different from other types of the indicia;
    an input device that inputs a command to the computer to reference any of the plurality of distinct dentally specific indicia to select a portion of the image to be modified, the selected portion being defined, at least in part, by one or more of the distinct dentally specific indicia referenced by the command; and
    at least one design tool that enables the selected portion to be modified in any of a plurality of directions,
    wherein the plurality of distinct dentally specific indicia include at least one of a preparation border, an equator, a marginal crest, and a fissure, and
    wherein, when the command references the preparation border, the selected portion extends from the preparation border to a center of an occlusal surface,
    wherein, when the command references the equator, the selected portion is located between the preparation border and the marginal crest,
    wherein, when the command references the marginal crest, the selected portion extends from the equator to the center of the occlusal surface, and
    wherein, when the command references the fissure, the selected portion is the occlusal surface delimited by the marginal crest.

2. The CAD system according to claim 1, wherein the plurality of distinct dentally specific indicia include a plurality of dentally specific lines.

3. The CAD system according to claim 1, wherein the plurality of distinct dentally specific indicia include a plurality of dentally specific points.

4. The CAD system according to claim 1, wherein the plurality of distinct dentally specific indicia include one or more dentally specific lines and one or more dentally specific points.

5. The CAD system according to claim 1, wherein a selection is made by selecting a region between at least two of the plurality of distinct dentally specific indicia.

6. The CAD system according to claim 1, wherein the image of the dental restoration body includes the preparation border.

7. The CAD system according to claim 6, wherein a selection is made by selecting a region between the preparation border and at least one of the plurality of distinct dentally specific indicia.

8. The CAD system according to claim 1, wherein the computer directs the display device to display a plurality of symbols, each of the plurality of symbols representing a design tool.

9. An imaging processing method comprising the steps of:
providing an image of a dental restoration body, the image of the dental restoration body including a plurality of distinct dentally specific indicia, each indicium being a single, selectable, unique type of dental feature that is different from other types of the indicia;
accepting an input command to reference any of the plurality of distinct dentally specific indicia to select a portion of the image to be modified, the selected portion being defined, at least in part, by one or more of the distinct dentally specific indicia referenced by the command; and
modifying the selected portion with a design tool, the design tool enabling the selected portion to be modified in any of a plurality of directions,
wherein the plurality of distinct dentally specific indicia include at least one of a preparation border, an equator, a marginal crest, and a fissure, and
wherein, when the command references the preparation border, the selected portion extends from the preparation border to a center of an occlusal surface,
wherein, when the command references the equator, the selected portion is located between the preparation border and the marginal crest,
wherein, when the command references the marginal crest, the selected portion extends from the equator to the center of the occlusal surface, and
wherein, when the command references the fissure, the selected portion is the occlusal surface delimited by the marginal crest.

10. The image processing method according to claim 9, wherein the plurality of distinct dentally specific indicia include a plurality of dentally specific lines.

11. The image processing method according to claim 9, wherein the plurality of distinct dentally specific indicia include a plurality of dentally specific points.

12. The image processing method according to claim 9, wherein the plurality of distinct dentally specific indicia include one or more dentally specific lines and one or more dentally specific points.

13. The image processing method according to claim 9, wherein a selection is made by selecting a region between at least two of the plurality of distinct dentally specific indicia.

14. The image processing method according to claim 9, wherein the image of the dental restoration body includes the preparation border.

15. The image processing method according to claim 14, wherein a selection is made by selecting a region between the preparation border and at least one of the plurality of distinct dentally specific indicia.

16. A computer-aided design (CAD) system comprising:
means for displaying an image of a dental restoration body, the dental restoration body including a plurality of distinct dentally specific indicia, each indicium being a single, selectable, unique type of dental feature that is different from other types of the indicia;
means for inputting a command to reference any of the plurality of distinct dentally specific indicia to select a portion of the image to be modified, the selected portion being defined, at least in part, by one or more of the distinct dentally specific indicia referenced by the command; and
at least one design tool that enables the selected portion to be modified in any of a plurality of directions,
wherein the plurality of distinct dentally specific indicia include at least one of a preparation border, an equator, a marginal crest, and a fissure, and
wherein, when the command references the preparation border, the selected portion extends from the preparation border to a center of an occlusal surface,
wherein, when the command references the equator, the selected portion is located between the preparation border and the marginal crest,
wherein, when the command references the marginal crest, the selected portion extends from the equator to the center of the occlusal surface, and
wherein, when the command references the fissure, the selected portion is the occlusal surface delimited by the marginal crest.

* * * * *